United States Patent
Riza et al.

(10) Patent No.: US 7,180,602 B2
(45) Date of Patent: Feb. 20, 2007

(54) AGILE SPECTRAL INTERFEROMETRIC MICROSCOPY

(75) Inventors: Nabeel Agha Riza, Oviedo, FL (US); Frank Perez, Tujunga, CA (US); Amana Bokhari, Oviedo, FL (US)

(73) Assignees: Nuonics, Inc., Winter Park, FL (US); University of Central Florida, Orlando, FL (US)

( * ) Notice: Subject to any disclaimer, the term of this patent is extended or adjusted under 35 U.S.C. 154(b) by 243 days.

(21) Appl. No.: 11/009,400

(22) Filed: Dec. 10, 2004

(65) Prior Publication Data

US 2005/0167578 A1 Aug. 4, 2005

Related U.S. Application Data

(60) Provisional application No. 60/528,868, filed on Dec. 11, 2003.

(51) Int. Cl.
*G01B 9/02* (2006.01)
(52) U.S. Cl. ............................ 356/484; 356/477
(58) Field of Classification Search .......... 356/451, 356/477, 484, 485, 486, 487, 491, 515, 517
See application file for complete search history.

(56) References Cited

U.S. PATENT DOCUMENTS

| | | | |
|---|---|---|---|
| 5,694,216 A | 12/1997 | Riza | |
| 5,864,403 A | 1/1999 | Ajji et al. | |
| 5,903,358 A * | 5/1999 | Zare et al. | 356/437 |
| 6,037,579 A * | 3/2000 | Chan et al. | 250/216 |
| 6,157,448 A | 12/2000 | Kowa et al. | |
| 6,243,168 B1 * | 6/2001 | Heflinger et al. | 356/486 |
| 6,473,179 B1 | 10/2002 | Wang et al. | |

* cited by examiner

*Primary Examiner*—Gregory J. Toetley, Jr.
*Assistant Examiner*—Michael A. Lyons
(74) *Attorney, Agent, or Firm*—James H. Beusse; Beusse Wolter Sanks Mora & Maire, P.A.

(57) ABSTRACT

An agile optical sensor based on spectrally agile heterodyne optical interferometric confocal microscopy implemented via an ultra-stable in-line acousto-optic tunable filter (AOTF) based interferometer using double anisotropic acousto-optic Bragg diffraction. One embodiment uses a tunable laser as the light source while other embodiments use a broadband source or a fixed wavelength laser as the source. One embodiment uses anisotropic diffractions in an AOTF to generate two near-collinear orthogonal linear polarization and slightly displaced beams that both pass via a test sample to deliver highly sensitive sample birefringence or material optical retardation measurements. A spherical lens is used to form focused spots for high resolution spatial sampling of the test object. The laser and AOTF tuning allows birefringence measurements taken at different wavelengths, one at a time. An alternate embodiment makes use of anisotropic diffractions in an acousto-optic deflector or Bragg cell instead of the wavelength tunable AOTF. The instrument also forms a classic interferometric confocal microscope via the use of single mode fiber optics or spatial filter pin-hole with a point photodetector for the receive light. An alternate embodiment via a transmissive beam generation design provides collinear co-located beams on the sample plane for super-accurate measurements.

4 Claims, 8 Drawing Sheets

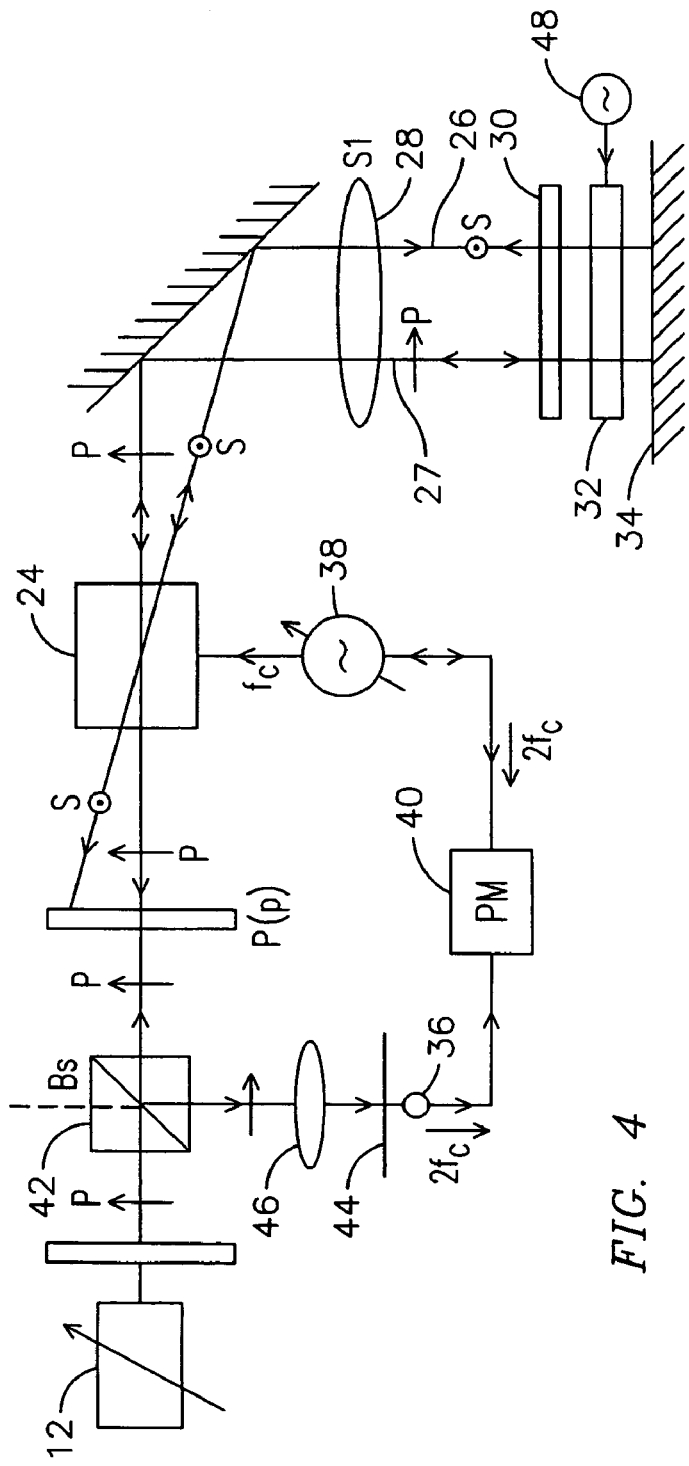
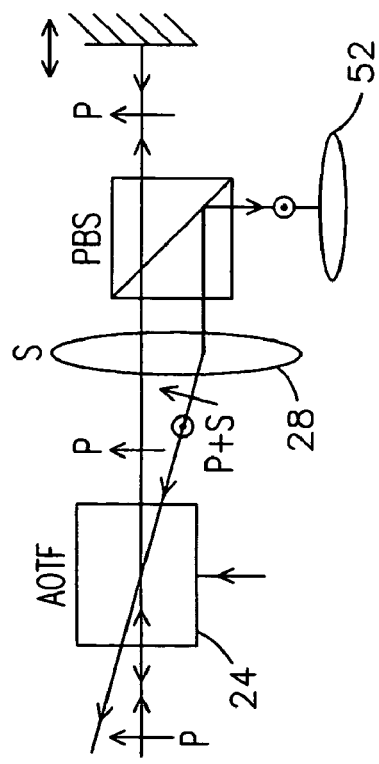
FIG. 4
FIG. 5A

US 7,180,602 B2

AGILE SPECTRAL INTERFEROMETRIC MICROSCOPY

SPECIFIC DATA RELATED TO THE INVENTION

This application claims the benefit of U.S. Provisional Application No. 60/528,868 filed on Dec. 11, 2003.

BACKGROUND OF THE INVENTION

The present invention relates to optical sensors and, more particularly, to optical sensors using heterodyne optical interferometry to implement confocal microscopy.

Well known works that use heterodyne interferometry to make birefringence measurements are described in J. Mackey, et.al., Meas. Sci. Technol. 10(1999) 946–955; B. Wang, e.al., U.S. Pat. No. 6,473,179B1, Oct. 29, 2002; F. Modine, et.al, Applied Optics, 14,3, March 1975; B. Wang, Optical Engg., 41,5, May 2002; B. Wang, Rev. Scientific Instru. Vol. 70,10, October 1999; H. Kowa, et.al., U.S. Pat. No. 6,157,448, Dec. 5, 2000; A. Ajji,et.al, U.S. Pat. No. 5,864,403, Jan. 26, 1999; C. Chou et.al, J. Opt. Soc. Amer. A, 14,6, June 1997; C. Chou, et.al, Applied Optics, 42,24, Sep. 1, 2003.

Works in heterodyne confocal microscopy include L-C Peng, et.al., Optics Lett., Vol. 26,6, March 2001. Works in confocal polarization microscopy include J. Bueno, et.al., Optics Lett., Vol. 27, No. 10, May 15, 2002; L. Yang, et.al., Applied optics, Vol. 42,28, 1 Oct., 2003; H. King, et.al. Optics Lett., 18,22, Nov. 15, 1993; P. Gleyzes, et.al., Optics Lett., 22,20, Oct. 15, 1997.

Works in spectral interferometry include: M. Raab et.al., J. Opt. Soc. Am. B, Vol. 2,9, September 1985; M. Shlyagin, et.al, Optics Lett., 20,8, Apr. 15, 1995; T. Fukano et.al., Optics Lett., 25,8, Apr. 15, 2000; Y. Watanabe et.al., Applied Optics, 41,13, 1 May 2002; C. Hitzenberger, et.al., Optics Express, 9,13, Dec. 17 2001; A. Vakhtin et.al, Applied optics, 42,34, 1 Dec. 2003; M. Choma et.al., Optics Express, 11,18, 8 Sept., 2003; R. Leitgeb, et.al., Optics Express, 11,8, 21 Apr. 2003; J. de Boer, et.al., Optics Lett., Vo. 28, No. 21, Nov. 1, 2003; S. Yun, et.al., Optics Express, Vol. 22, 11, 3 Nov., 2003; G. Hausler et.al., J. Biomedical Optics, 3,1, January 1998; R. Leitgeb, et.al, Optics Express, 11,23, 17 Nov. 2003; A. Fercher et.al., Optics Comm., 117, 43–48, 15 May 1995.

Earlier, for example, acousto-optic deflectors or Bragg cells using isotropic Bragg diffraction have been used to form scanning heterodyne interferometers such as in N. A. Riza, "Scanning heterodyne acousto-optical interferometers," U.S. Pat. No. 5,694,216, Dec. 2, 1997; N. A. Riza, "In-Line Acousto-Optic Architectures for Holographic Interferometry and Sensing," *OSA Topical Meeting on Holography Digest*, pp. 13–16, Boston, May, 1996; N. A. Riza, "Scanning heterodyne optical interferometers," *Review of Scientific Instruments*, American Institute of Physics Journal, Vol. 67, pp. 2466–2476 7, Jul. 1996; and N. A. Riza and Muzamil A. Arain, "Angstrom-range optical path-length measurement with a high-speed scanning heterodyne optical interferometer," Applied Optics, OT, Vo. 42, No. 13, pp. 2341–2345, 1 May 2003. These interferometers use the changing RF (radio frequency) of the AOD or isotropic Bragg cell drive to cause a one dimensional (1-D) scanning beam but perform optimally only for a given design wavelength.

BRIEF DESCRIPTION OF THE DRAWINGS

FIG. 4 illustrates still another embodiment of the spectrally agile heterodyne optical interferometric confocal microscope using transmit/receive free-space optics and a x-y scanning mirror.

FIG. 5a illustrates an optional three-dimensional drive system for positioning the sample;

DETAILED DESCRIPTION OF THE INVENTION

Figure 1:
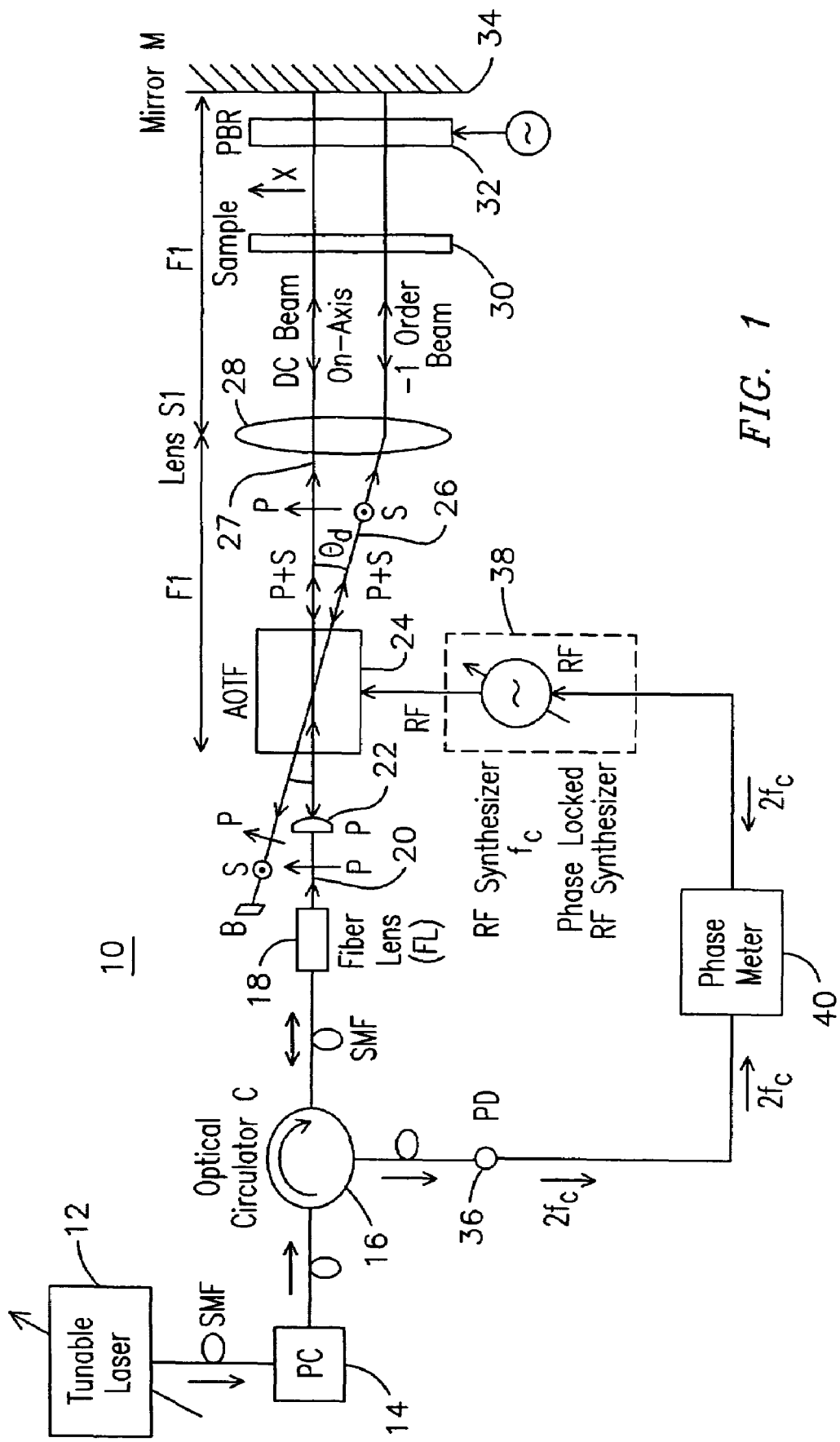
FIG. 1 illustrates a first embodiment of the spectrally agile heterodyne optical interferometric confocal microscope sensor instrument using transmit/receive fiber-optics.

It is well known that heterodyne optical interferometry can be used to detect very small changes in optical properties of a material (e.g., refractive index, material thickness). These changes can be man-made such as on a phase-encoded optical security card or environmentally induced such as by temperature changes in a jet engine. Heterodyne interferometry can also be used to take optical retardation or material birefringence measurements when using polarization interference microscopy where two orthogonal linear polarizations pass through a sample. In addition, spectral interferometry is a useful measurement tool when sensing data is required for several independent wavelengths.

The present invention introduces an instrument that combines many of the independent features of previous techniques to realize a "heterodyne spectral interferometric confocal microscope." There are numerous applications for heterodyne spectral interferometric confocal microscopy that include material birefringence measurements, such as, for example, biomedical imaging using Fourier transform (FT) spectral interferometry (or FT OCT: Optical Coherence Tomography), refractive index or optical path length change measurements for environmental sensing, and real-time non-invasive monitoring of biological and chemical structures.

In the present invention, an agile optical sensor or instrument is based on spectrally agile heterodyne optical interferometric confocal microscopy implemented via an ultra-stable in-line acousto-optic tunable filter (AOTF) based interferometer using double anisotropic acousto-optic Bragg diffraction. In effect, the key principles exploited are use of linearly polarized input light and its two anisotropic acousto-optic Bragg diffractions and general undiffracted light transmission through a single anisotropic material acousto-optic (AO) device that enables the following: (a) spatial filtering of unwanted light by angular beam displacement and translational beam displacement, (b) Linear polarization switching of the desired signal light, (c) Doppler shifting of the desired signal light to generate an RF heterodyne carrier, (d) Use of polarization filtering to clean signal light and block unwanted polarization (i.e., noise beams with unwanted orthogonal linear polarization), (e) Generation of the final collinear on-axis signal beam pair (one with zero Doppler shift and another with Doppler shift) to generate highly stable RF heterodyne signal, and (f) Implementation of confocal microscopy by use of single mode fiber-optics or free-space pin-hole spatial filter optics in the optical sensor instrument design. A first embodiment uses a tunable laser as the light source while other embodiments use a broadband source or a fixed wavelength laser as the source. The first embodiment uses anisotropic diffractions in an AOTF to generate two near-collinear orthogonal linear polarization and slightly displaced beams that both pass via the test sample to deliver highly sensitive sample birefringence or material optical retardation measurements. A spherical lens is used to form focused spots for high resolution microscopic spatial sampling of the test object. The laser and AOTF tuning allows birefringence measurements taken at different wavelengths, one at a time. Other embodiments make use of anisotropic diffractions in an anisotropic crystal-based acousto-optic deflector or Bragg cell instead of the wavelength tunable AOTF. The instrument also forms a classic interferometric confocal heterodyne microscope via the use of single mode fiber optics or spatial filter pin-hole with a high speed (e.g., 80 MHz) point photo-detector for the receive light. Both fiber-optic and free-space optic feed and receiver designs for the instrument are disclosed. High speed tuning (milliseconds to nanoseconds) of the laser along with no-moving parts high speed (e.g., microseconds) spectral filtering/tuning via the AOTF give powerful new spectral processing attributes for the optical sensor instrument such as implementation of high speed FT OCT or Two photon fluorescence microscopy. Still another embodiment uses a transmissive beam generation design to provide collinear co-located beams on the sample plane for super-accurate measurements.

Figure 2A:
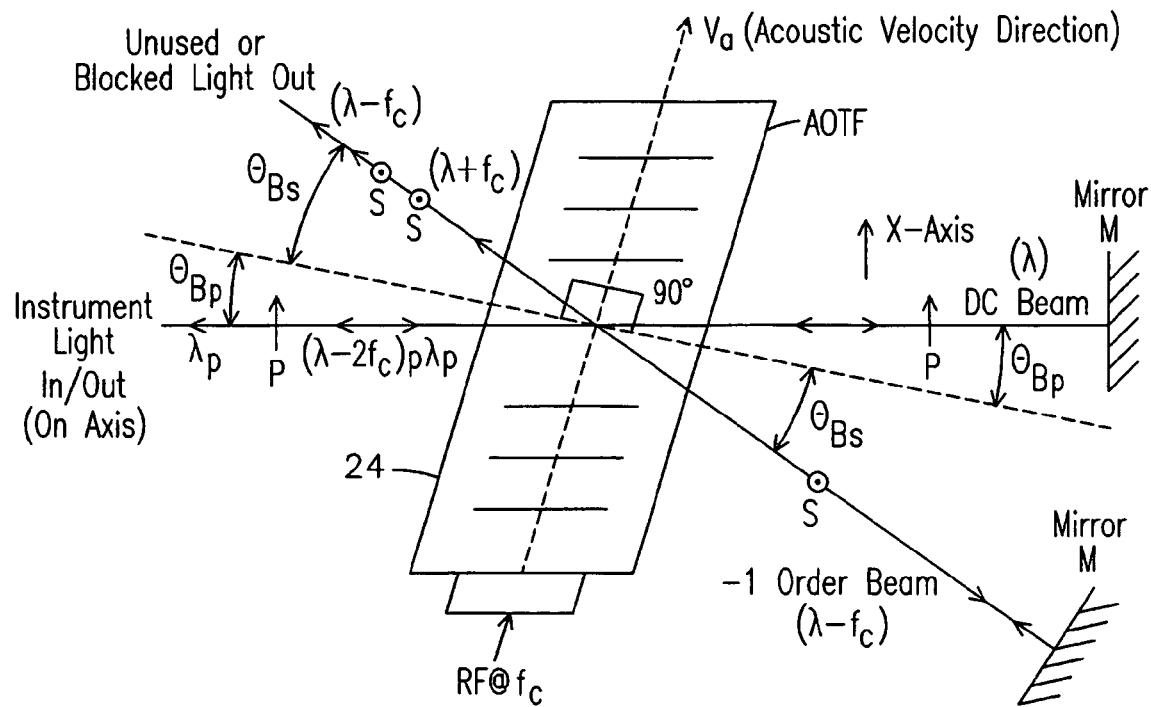
FIG. 2a illustrates one form of AOTF light beam operation used in the instrument of FIG. 1.
Figure 2B:
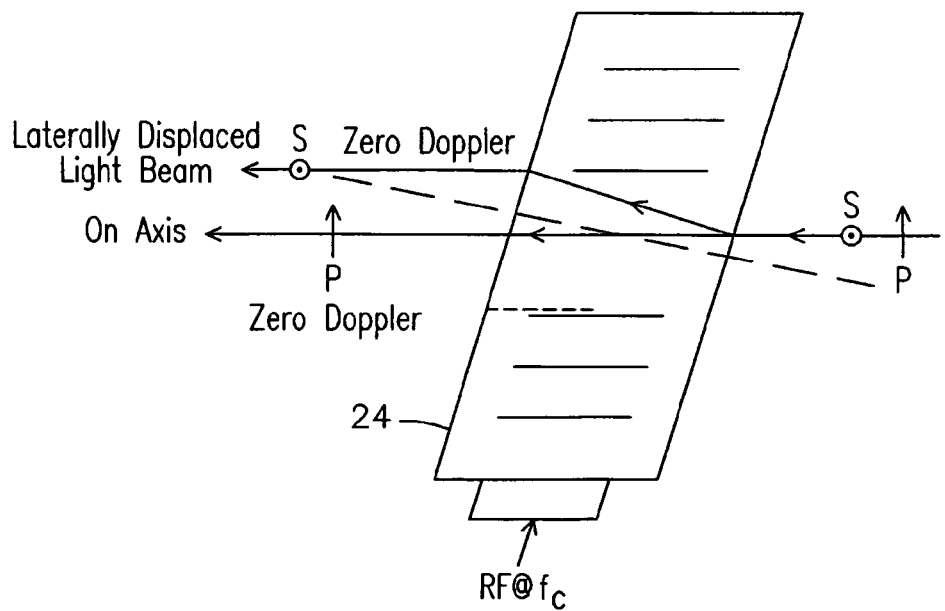
FIG. 2b illustrates light paths for an anisotropic material.

FIG. 1 shows one embodiment of a spectrally agile heterodyne optical interferometric confocal microscope or instrument 10 using transmit/receive fiber-optics. The birefringent sample must be equivalent to being sandwiched between two parallel optically transmissive plates (e.g., glass plates with a liquid crystal layer) between the locations of the two probing beams passing through the sample. Light from a fiber-coupled tunable laser 12 passes through a fiber-optic polarization controller (PC) 14 to enter a 3-port fiber-optic circulator 16 that feeds a single mode fiber (SMF) coupled Fiber Lens (FL) 18 that produces a collimated laser beam 20 in freespace. The single mode fiber SMF provides optical coupling between each of the elements identified above. The PC 14 is tuned so that the freespace laser beam 20 is p-polarized (or horizontal or x-direction polarized). This p-polarized beam 20 passes via a high extinction ratio polarizer 22 aligned to let p-polarization light pass. This p-polarized light beam 20 enters an AOTF 24 that is Bragg matched such that the p-polarized input light beam generates an s-polarized (vertical or y-direction polarization) negative Doppler shifted −1 order diffracted beam 26 and a DC beam 27. FIG. 2a shows an embodiment of the AOTF 24 and its effect on beam 20. The illustrated AOTF is a non-collinear device. FIG. 2a shows diffractions, polarization directions, and Doppler shifts when no sample is placed in the instrument, i.e., just using mirrors for reflections for both beams produced by the AOTF when p-polarized (horizontal) light is input to the AOTF. Similar beam operations and layout is obtained using a collinear AOTF device. By controlling the RF drive power and frequency of the AOTF drive, the AOTF diffraction efficiency and diffraction wavelength is selected so as to match the tunable laser wavelength for transmit mode operations of the instrument. The undiffracted or DC light from the AOTF stays p-polarized and without a Doppler shift. The −1 order light gets a Doppler shift equal to the RF drive frequency fc. Referring again to FIG. 1, the two near collinear orthogonal linear polarization beams are made collinear but spatially separated by a focusing lens 28 of focal length F1. The sample 30, Programmable Bias Retarder (PBR) 32, and reference mirror 34 all are placed very near the focal plane of spherical lens 28. The two beams form focused spots on this focal plane and hence act as point spatial functions to measure optical properties of the placed sample. Note that the birefringent sample must be equivalent to being sandwiched between two parallel optically transmissive plates (e.g., glass plates with a liquid crystal layer) between the locations of the two probing beams passing through the sample. This is because both beams must suffer the same optical path lengths, except for the much smaller change in path lengths due to the material birefringence. Because the beams go through the sample twice, the eventual raw data measures twice the birefringence of the sample, producing a factor of 2 improved sensitivity instrument versus a transmissive only instrument. FIG. 2b shows the microscope instrument 10 design coordinates with respect to an optical Fast Axis (FA) of the sample 30 with an unknown birefringence. The AOTF light beam operations used in the microscope 10 has on-axis s-polarized light traveling from right to left into the AOTF. It is shown that due to the anisotropic nature of the AOTF crystal material, the s-polarized light suffers a lateral displacement after exiting the AOTF, this making this light no longer on-axis and collinear (one on top of the other) with the original on axis-polarized input light. The FA is measured from the instrument x-axis and is given by the anticlockwise measured positive angle Ø where Ø is the retardation of the sample. If Ø is negative, the Slow Axis (SA) is horizontal (or x-direction) and the FA vertical (or y-direction).

A polarized light beam with its x (or p) and y (or s) electric field components after one pass through the retardation plate 32 is given by the vector:

$$\begin{bmatrix} E'_x \\ E'_y \end{bmatrix} = W(\varphi, \Gamma) \begin{bmatrix} E_x \\ E_y \end{bmatrix} \text{ where}$$

$$W(\varphi, \Gamma) = \begin{bmatrix} \cos(-\varphi) & \sin(-\varphi) \\ -\sin(-\varphi) & \cos(-\varphi) \end{bmatrix} \begin{bmatrix} \exp(-i\Gamma/2) & 0 \\ 0 & \exp(i\Gamma/2) \end{bmatrix} \begin{bmatrix} \cos\varphi & \sin\varphi \\ -\sin\varphi & \cos\varphi \end{bmatrix}$$

Because of the reflection of the probe beams 26, 27 from the mirror 34, the instrument reference (DC) 27 and signal 26 (−1 order) beams will pass twice through the sample 30, in effect giving twice the sample retardation that allows the retardation matrix to be rewritten as:

$$W(\varphi, \Gamma) = \begin{bmatrix} \exp(-i\Gamma)\cos^2\varphi + \exp(i\Gamma)\sin^2\varphi & \exp(-i\Gamma)\cos\varphi\sin\varphi - \exp(i\Gamma)\cos\varphi\sin\varphi \\ \exp(-i\Gamma)\cos\varphi\sin\varphi - \exp(i\Gamma)\cos\varphi\sin\varphi & \exp(-i\Gamma)\sin^2\varphi + \exp(i\Gamma)\cos^2\varphi \end{bmatrix}$$

The incoming beams into the sample in the instrument 10 of FIG. 1 are the horizontally or p-polarized (DC) beam 27 written as the vector $$\begin{bmatrix} 1 \\ 0 \end{bmatrix},$$

and the vertically or s-polarized (−1 order diffracted) beam 26 written as the vector $$\begin{bmatrix} 0 \\ 1 \end{bmatrix}.$$

So after the double pass through the sample, the DC or reference beam 27 becomes the electric field vector:

$$\begin{bmatrix} 1 \\ 0 \end{bmatrix} \to \begin{bmatrix} E'_{x1} \\ E'_{y1} \end{bmatrix} = W(\varphi, \Gamma) \begin{bmatrix} 1 \\ 0 \end{bmatrix} = \begin{bmatrix} \exp(-i\Gamma)\cos^2\varphi + \exp(i\Gamma)\sin^2\varphi \\ \exp(-i\Gamma)\cos\varphi\sin\varphi - \exp(i\Gamma)\cos\varphi\sin\varphi \end{bmatrix},$$

while the −1 order or Doppler shifted signal beam becomes the electric field vector:

$$\begin{bmatrix} 0 \\ 1 \end{bmatrix} \to \begin{bmatrix} E'_{x2} \\ E'_{y2} \end{bmatrix} = W(\varphi, \Gamma) \begin{bmatrix} 0 \\ 1 \end{bmatrix} = \begin{bmatrix} \exp(-i\Gamma)\cos\varphi\sin\varphi - \exp(i\Gamma)\cos\varphi\sin\varphi \\ \exp(-i\Gamma)\sin^2\varphi + \exp(i\Gamma)\cos^2\varphi \end{bmatrix}$$

Note that the signal and reference beams 26, 27 now both contain both s (or y-direction) and p (or x-direction) polarization components. So far, this analysis assumes that the AOTF 24 is driven for a 50:50 input light split such that 50% of input light is diffracted and the remaining 50% light stays in the DC or undiffracted beam 27. Note that by controlling the AOTF drive power, this split ratio can be optimized for a desired value.

The AOTF 24 only diffracts linearly polarized light if it is incident at the matching Bragg angle for this specific polarization. By examining FIG. 1 and FIGS. 2a, 2b), one can see that this condition has a unique effect for the returning −1 order signal beam and the on-axis returning zero Doppler DC beam. Specifically, only the s component of the returning −1 order is correctly Bragg matched with the AOTF and hence this s-component correctly undergoes Bragg diffraction that converts the input s-light to a p-polarized −1×−1 double negative Doppler diffracted beam that is now on-axis with the original p-polarized input beam to the AOTF. In effect, this −1×−1 order p-polarized beam can enter the SMF fiber lens 18 for transmission to the circulator 16 and then photodiode diode (PD) 36 for eventual heterodyne detection with the returning reference beam. Hence, the returning p-polarized signal −1×−1 order beam entering the fiber lens can be written as the electric field with only one component, namely the p-polarized component given by:

$$E1x = a1\{\exp(-i\emptyset)\sin^2\emptyset + \exp(i\emptyset)\cos^2\emptyset\}.$$

The diffraction efficiency for the AOTF 24 for this second diffraction pass is assumed as a1. Note that the undiffracted (1−a1) part of the s-polarized −1 order beam component passes as s-polarized light through the AOTF (right to left on FIG. 1) and becomes off-axis (due to angular displacement) with the fiber lens position and hence does not enter the fiber lens 18 and thus the PD 36. Moreover, the polarizer 22 between the AOTF 24 and fiber lens 18 will also block this return off-axis s-polarized light.

For the case of the returning on-axis reference DC beam with no Doppler shift, both p and s components of this returning beam traveling right to left (in FIG. 1 and FIGS. 3–5) stay on-axis before the AOTF 24. In this case, only the p-component of the returning beam is Bragg matched for AOTF diffraction. Thus, this p-component undergoes some Bragg diffraction (factor of a1) and polarization switching to s-polarized light. Since this new s-polarized light is angularly displaced and off-axis, it will not enter the fiber lens 18. In addition, the polarizer 22 will block this s-polarized light. The remaining (1−a1) factor p-polarized reference zero Doppler shifted light stays on axis and enters the fiber lens 18 after passing through the polarizer 22. Hence, this returning on-axis p-polarized component of the reference zero Doppler shift light entering the fiber lens can be written as:

$$E2x = (1-a1)\{\exp(-i\emptyset)\cos^2\emptyset + \exp(i\emptyset)\sin_2\emptyset\}.$$

On the other hand, the s-polarized component of the returning zero Doppler shift eference beam is not Bragg matched to the AOTF 24 for s-polarized input beam diffraction. Hence, this returning s-polarized zero Doppler reference beam component suffers no AOTF diffraction. Nevertheless, as shown in FIG. 2b, this s-polarized light traveling from right to left into the AOTF gets laterally translated due to the anisotropic nature of the AOTF crystal material (much like via a Calcite Beam Displacing Prism:BDP). In effect, this unwanted s-polarized returning beam gets laterally displaced with respect to the input light axis, and hence cannot enter the on-axis lens 18. The AOTF design via its crystal dimensions is such that this unwanted s-polarized light is displaced such that it will completely miss the aperture of the fiber lens. Typically, this displacement is several millimeters (e.g., >3 mm) with a typical fiber lens diameter of 1.8 mm. Thus, even if no polarizer 22 is placed between fiber lens 18 and AOTF 24 in FIG. 1 (and FIG. 5), this unwanted E2y optical component does not enter the fiber-optics and is not detected by PD 36;, as the single mode fiber optics acts as a spatial filter that blocks the unwanted light. Another way to block this light is via pinhole type spatial filters such as used in the freespace design embodiments of the proposed instrument shown in FIGS. 3–4. If the polarizer 22 is used in the instrument designs (FIG. 1 and FIGS. 3–5), this E2y component which is s-polarized cannot pass the polarizer 22 into the fiber lens 18, making E2y=0. In addition, all other returning s-light is blocked by the polarizer 22. Note that FIG. 1 and FIGS. 3–5 do not show the displaced returning s-polarized beam that is traveling side-by-side with the on-axis p-beams. Typical angular beam displacement angles between the on-axis and diffracted beams for AOTF range in the 1 to 6 degrees range. Thus, the only beams that are also p-polarized and, that eventually enter the fiber lens (or reach the PD 36) are the (a) zero Doppler reference beam given by E2x=$E_2$ and the (b) 2fc Doppler shifted signal beam given by E1x=$E_1$, where fc is the AOTF RF frequency.

Figure 2C:
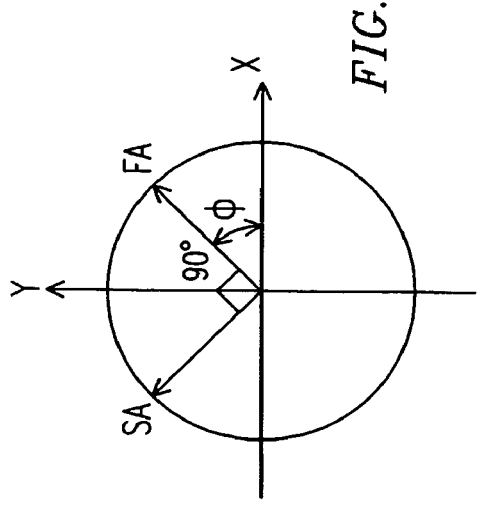
FIG. 2c illustrates coordinates with respect to the optical Fast Axis (FA) of a sample retarder with an unknown birefringence.

The signal and reference beam pair travels via the circulator 16 to the PD 36. The measured interferometric signal at an RF frequency 2fc generated by the photodetector is given by the expression: $2|E_1||E_2|\cos(\phi_1-\phi_2)$, where $\phi_1$ and $\phi_2$ are the phase values of the complex optical field components $E_1$ and $E_2$, respectively. The relative RF phase shift from the optical instrument is generated by using external phased locked RF synthesized signal generator 38 that produces an external RF reference signal at 2fc frequency that is fed to a lock-in amplifier/phase meter (PM) 40 along with the 2fc RF signal generated by the PD 36. AOTF drive frequency signal at fc is also generated by the phase-locked RF synthesizer 40. By observing and measuring both the amplitude and phase shift of the RF signal produced by the PD 36 for a given sample location and sample rotational position with respect to the instrument x (or p) and y(s) axes (see FIG. 2c), one can deduce the retardance value and hence birefringence of the sample.

Using the previously stated expressions for $E_1$ and $E_2$, the computed RF phase difference (FIG. 6) $\Delta\phi=\phi_1-\phi_2$ obtained via the photo-detector 36 and the RF amplitude (FIG. 7) measured by the photo detector given as A=2 times magnitude of $E_1$ times magnitude of $E_2$ are computer calculated. The phase difference (FIG. 6) in radians is calculated for various retardation values (e.g., $\pi/6$, $\pi/3$, $\pi/2$, $2\pi/3$, $5\pi/6$, and $\pi$) of a birefringent sample at various rotation angles of the sample 30 FA. Similarly, the amplitude of the RF signal is calculated and plotted for various retardation values (e.g., $\pi/6$, $\pi/3$, $\pi/2$, $2\pi/3$, $5\pi/6$, and $\pi$) of a birefringent sample. These plots indicate the procedure to be used when calculating the birefringence for a given sample placed in the microscope instrument. From the FIG. 7 amplitude signal plot, it is clear that when the sample is rotated through 180 degrees, the RF signal minima occur at two FA rotation angles of angle Ø=45 degrees and Ø=135 degrees. The only case this is not true is for the integer multiples of $\pi/2$ retardation cases, where it is necessary to introduce a known bias retardation offset via the programmable bias retardation (PBR) device 32 in FIG. 1 and FIGS. 3–5. The PBR 32 can be a parallel-rub nematic liquid crystal (NLC) electrically controlled phase cell where easily 0 to $N\pi$ retardations (e.g., N=5) can be electrically introduced to remove measurement ambiguity when the mentioned RF amplitude minima ambiguity occurs or when high orders of sample retardation (>$\pi$) are present. The PBR 32 is inserted with its FA (or SA) to align with the instrument 10 x (or y) axis or the other way around.

Figure 6:
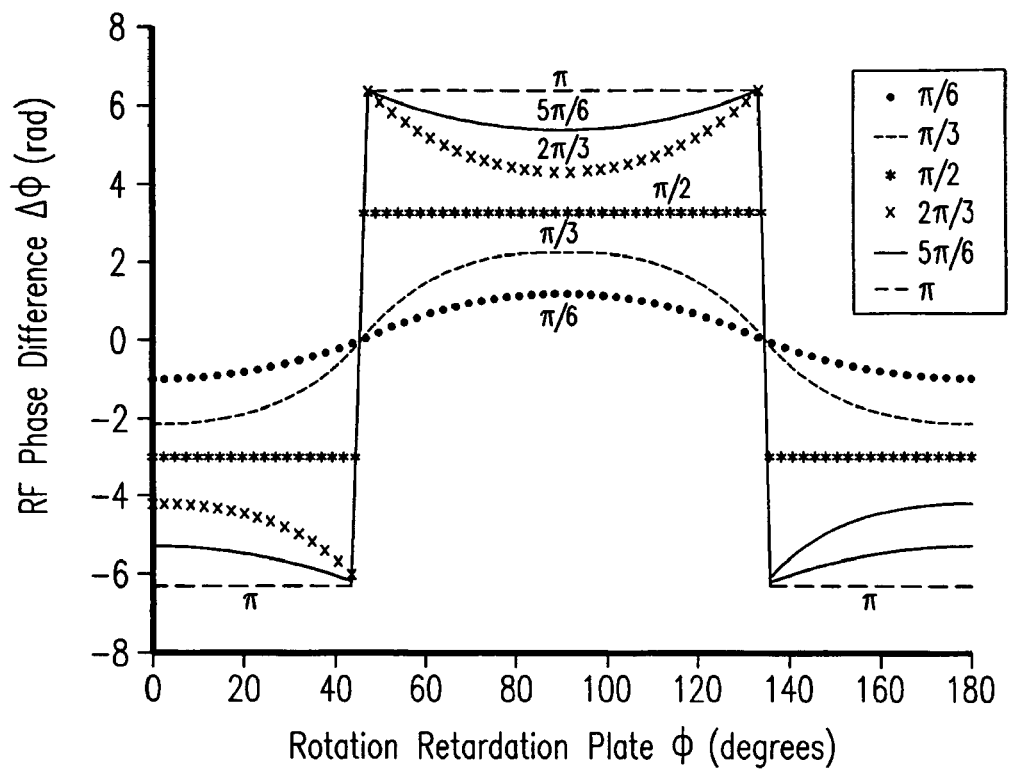
FIG. 6 illustrates computer calculated plots of the microscope RF phase difference in radians for various retardation values (e.g., $\pi/6, \pi/3, \pi/2, 2\pi/3, 5\pi/6$, and $\pi$) of a birefringent sample at various rotation angles of the sample FA.
Figure 7:
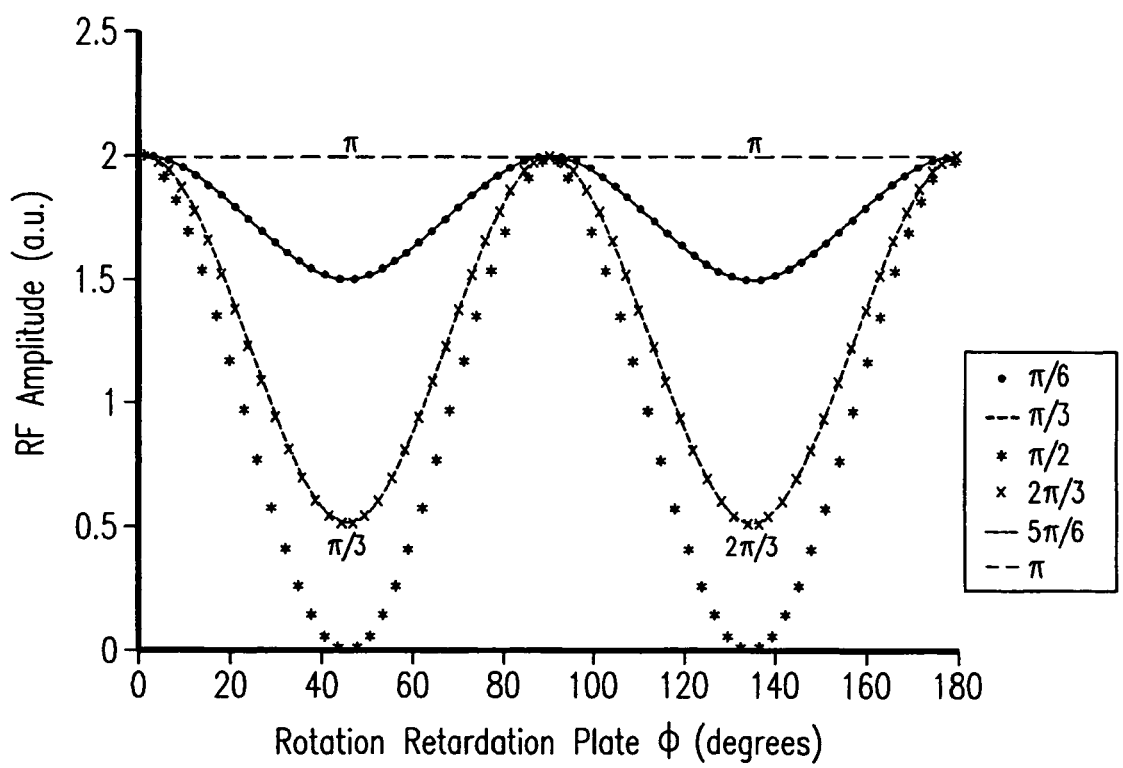
FIG. 7 illustrates computer calculated plots of the microscope output photodetector generated AC signal RF amplitude for various retardation values (e.g., $\pi/6, \pi/3, \pi/2, 2\pi/3, 5\pi/6$, and $\pi$) of a birefringent sample at various rotation angles of the sample FA.
Figure 8:
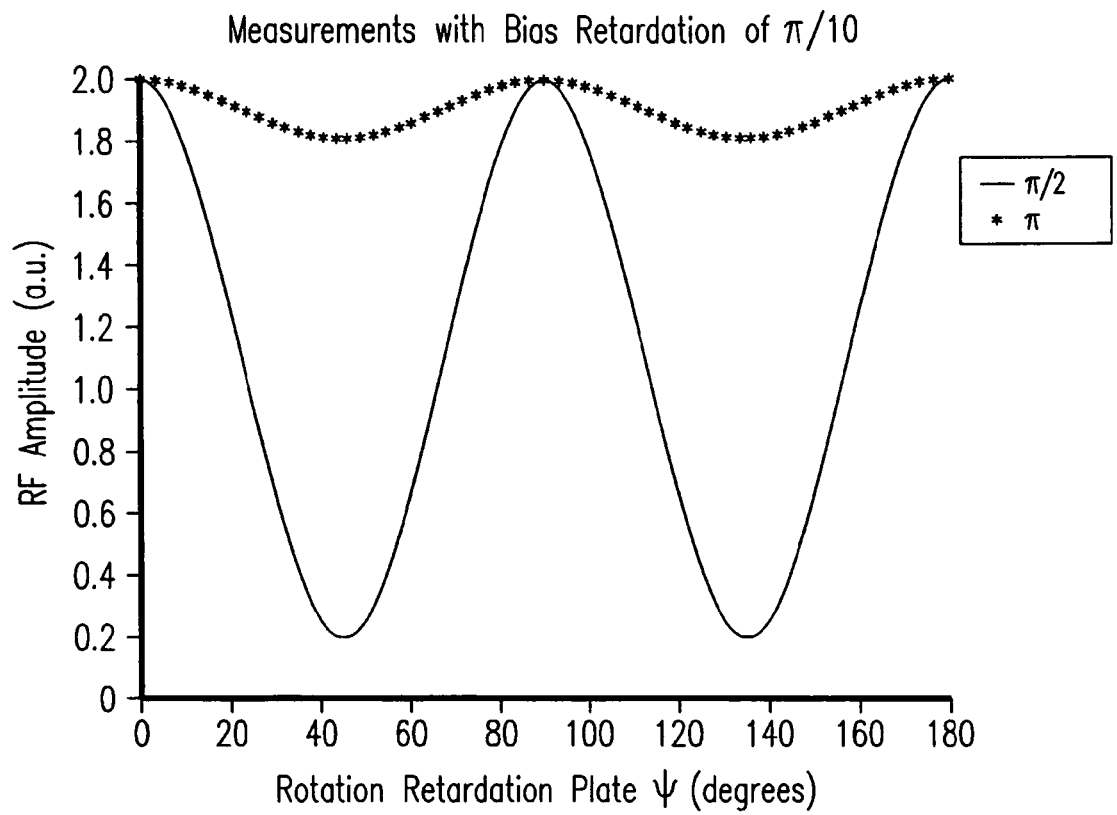
FIG. 8 illustrates computer calculated plots of the microscope output PD generated AC signal RF amplitude with an added $\pi/10$ reference retardation bias for the ambiguous retardation values of $\pi/2$ and $\pi$ of a birefringent sample at various rotation angles of the sample FA.
Figure 9:
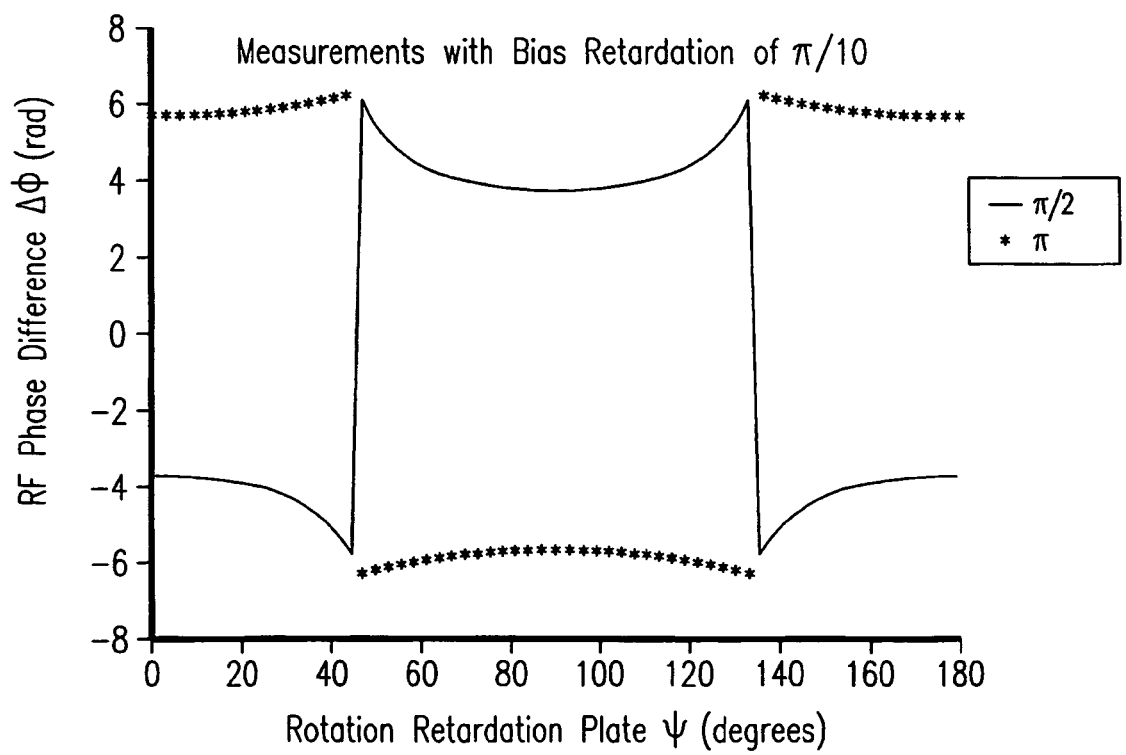
FIG. 9 illustrates computer calculated plots of the microscope RF signal phase difference with an added $\pi/10$ reference retardation bias for the ambiguous retardation values of $\pi/2$ and $\pi$ of a birefringent sample at various rotation angles of the sample FA.

FIGS. 8 and 9 show how the RF phase and RF amplitude plots change when a bias retardation is added for the original ambiguous cases of $\pi/2$ and $\pi$ retardation values, thereby again generating the two minima. Once the minima are known, then the sample FA or the SA location is known as it is 45 degrees from these minima angles. At this rotation location where now the sample FA or SA is aligned with the instrument 10 x (or y) axis, the RF phase shift is experimentally measured as the sample retardance in degrees or radians. Since the wavelength $\lambda$ is known, the sample retardance R can be converted to sample retardation in units of length (i.e., nanometers). Birefringence has units of retardation per unit path length of light, i.e., nanometer/centimeter. As the birefringent sample thickness d is known, the sample birefringence $\Delta n$ can be calculated, as RF Phase Shift=$(2\pi/\lambda) \Delta n$ d, where $\Delta n$ d is the retardance R. To know which angle or minima location marks the FA (or SA) of the sample, one must observe the phase data around the expected (45 degree offset from the minima angle location) to see if the phase is increasing or decreasing and match it to the FIG. 6 plot. Depending on which phase change effect happens, the chosen test axis location can be labeled as the sample FA or SA. Thus, the instrument 10 can successfully determined the given birefringent sample's retardation and direction of FA and SA. As the instrument is calibrated, one can also access the transmission efficiency of the material by measuring the amplitude of the RF signal. Because the FA/SA of the PBR 32 is known, one can also measure the sign of the retardation for cases of large retardation (>$\pi$). Fixed known value retardation plates can also be effectively used as fixed bias offsets instead of the programmable PBR if the sample retardations are known to avoid the ambiguous states of multiples of $\pi/2$ retardation. FA means direction of sample where refractive index is small so speed of light is faster compared to the other orthogonal direction in the sample where index is higher and hence speed of light is slower.

Figure 3:
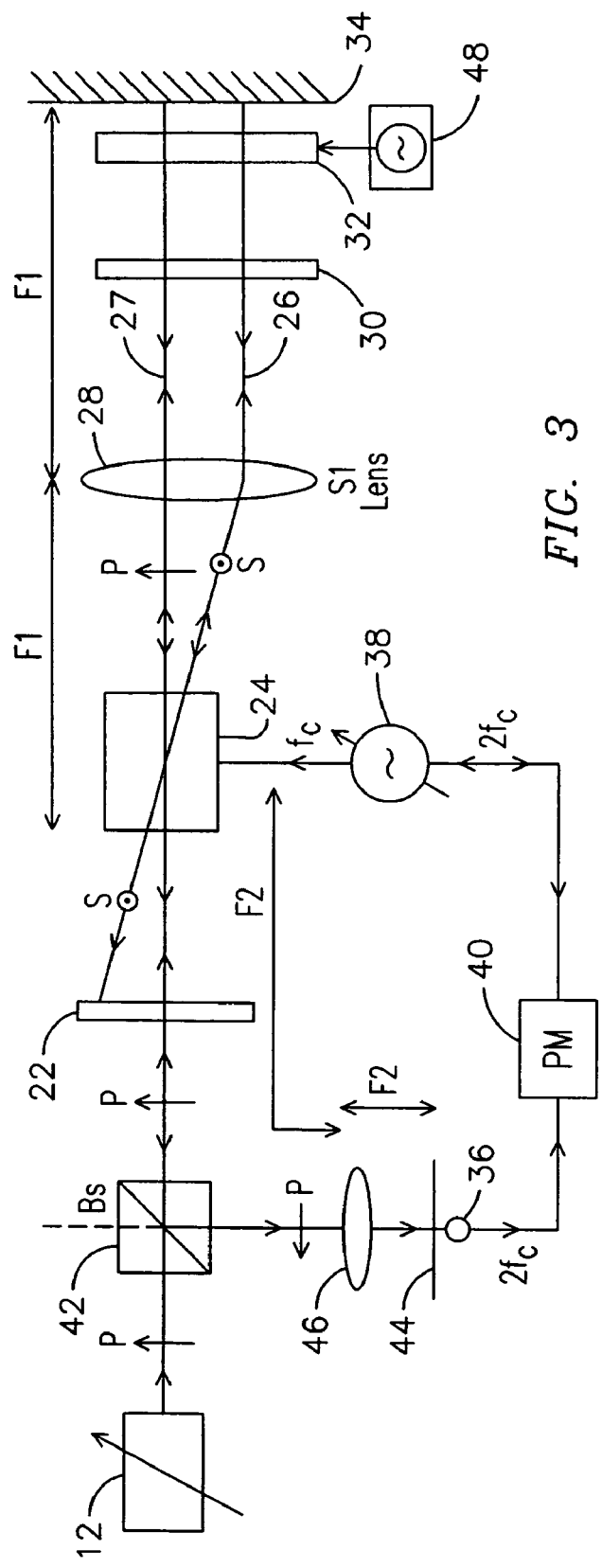
FIG. 3 illustrates another embodiment of the spectrally agile heterodyne optical interferometric confocal microscope using transmit/receive free-space optics.

FIG. 3 shows an alternate embodiment of the spectrally agile heterodyne optical interferometric confocal microscope 10 using transmit/receive free-space optics that include a cube beam splitter (BS) 42. The key point to note is the use of a pin-hole spatial filter 44 before the PD 36 to produce a confocal microscope and also block off any off-axis noise light. The lens 46 is added to produce this focused light, in effect producing an imaging condition between the PD 36 and the sample plane focused spot. Note that the sample 30 can be on a x-y-z translation stage indicated by block 48 to generate a scanned birefringence map of the sample area or volume.

Figure 5:
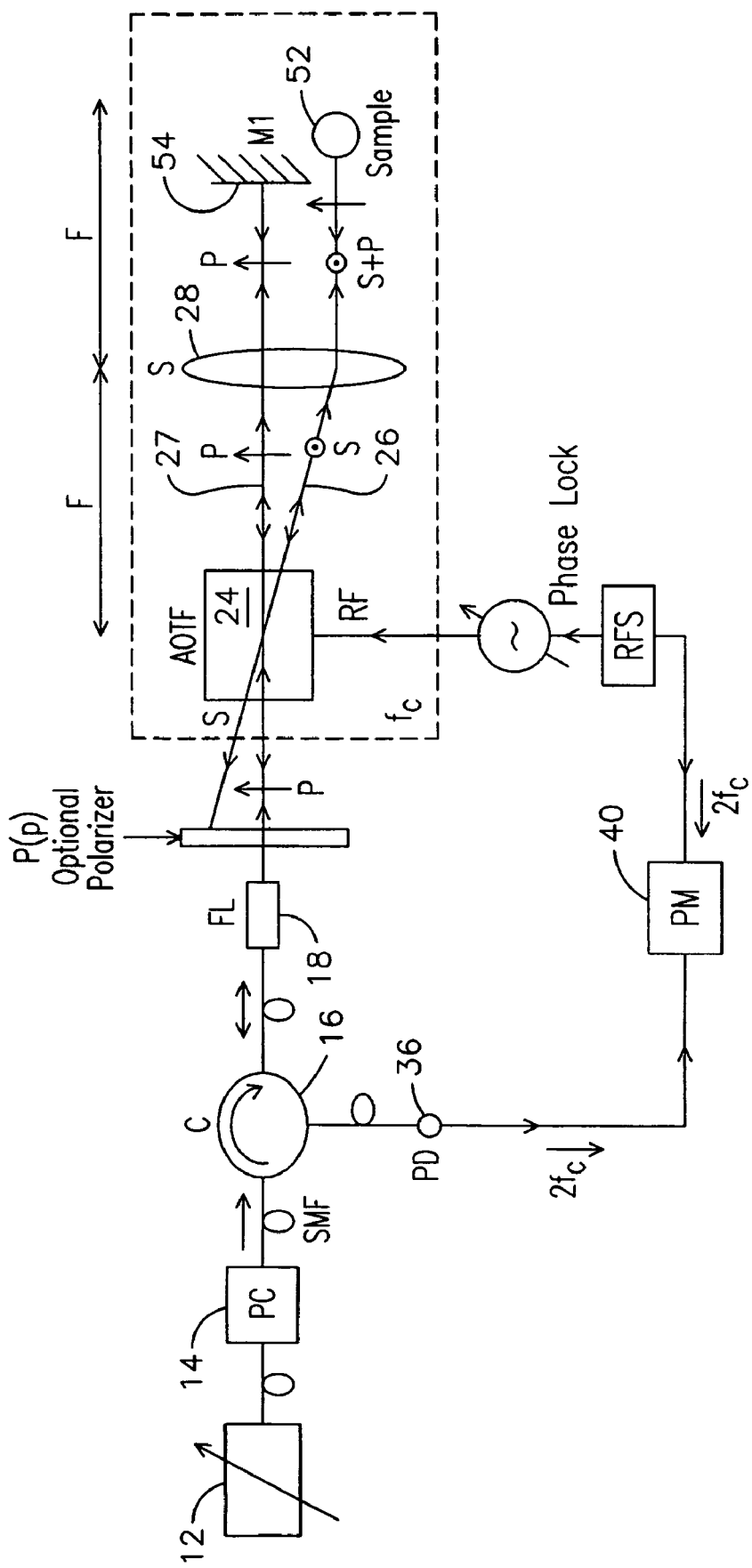
FIG. 5. illustrates an embodiment of the spectrally agile heterodyne optical interferometric confocal microscope using transmit/receive free-space optics and spatially independent sample and reference probing beams.

FIG. 4 shows another embodiment of the spectrally agile heterodyne optical interferometric confocal microscope 10 using transmit/receive free-space optics and an x-y scanning mirror 50 to scan the sample 30 with the two probe beams 26, 27 so that the sample does not need to be translated. However, the sample can be rotated as indicated by block 50. FIG. 5 shows still another embodiment of the spectrally agile heterodyne optical interferometric confocal microscope 10 using transmit/receive free-space optics and spatially independent sample and reference probing beams 26, 27. This approach is effective particularly if the birefringent sample 52 is not spatially uniform in thickness outside the beam size. In addition, this design acts as a general heterodyne interferometer where one beam hits a reference mirror 54 (fixed or movable) and the second beam independently hits the sample 52 under test. A polarization beam splitter (PBS) 56 can also be used to separate the two probe beams 26, 27 as seen in FIG. 5a.

It is noted that the instrument 10 can take data on a per wavelength basis across a specified band. In effect, it becomes a spectroscopy tool. The per wavelength data can also be Fourier transformed electronically to implement FT OCT. Wavelength scanning interferometry approaches can also yield additional data, such as when analyzing high order retardations. The light sources that can be used include the preferred tunable laser, but others can also be used including fixed wavelength lasers or broadband lasers. Other non-laser source options are also possible, but with system constraints such as related to SMFs and confocal optics. The light sources and the AOTF can also be temporally modulated (e.g., time gated) to implement new sample probing capabilities such as in two photon imaging and other florescence imaging techniques. Note that the AOTF is a narrowband wavelength filter that can be tuned to let the chosen light wavelength (or wavelengths) onto the sample or into the photodetector. Also note that an anisotropic acousto-optic (AO) deflector or anisotropic AO material Bragg cell can also be used instead of the AOTF in the illustrated designs. In this case, the instrument wavelength band of operations is limited. Based on optical sources and AOTFs available, a broad spectrum of wavelengths can be covered from the ultraviolet (UV), visible, near infrared (IR) to far IR. Both non-collinear type and collinear type AOTFs can be used with the instrument 10. The microscope 10 can have a great impact in many applications ranging from biomedical optics to liquid crystal testing.

Figure 10:
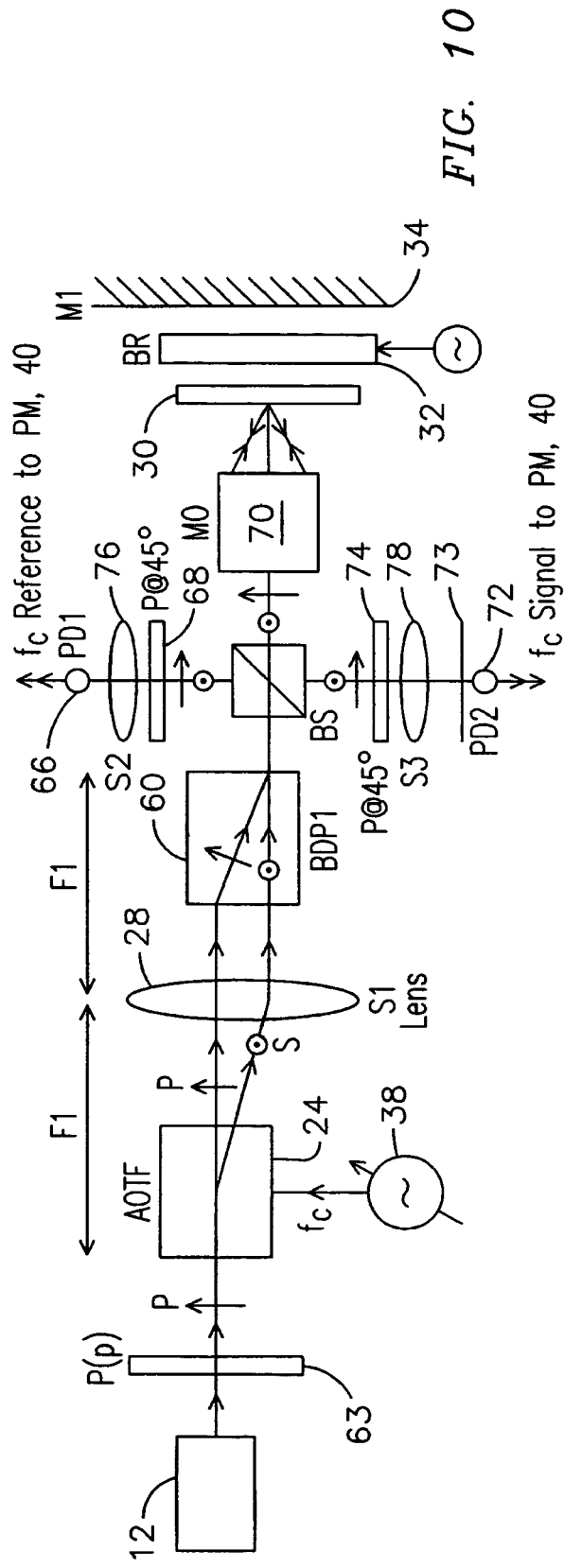
FIG. 10 illustrates an embodiment of a spectrally agile heterodyne optical interferometric confocal microscope using a polarization beam displacement prism (BDP) to make beam collinear and collocated at the sample plane.

In the described heterodyne microscope 10 designs, the two orthogonal linear polarized beams 26, 27 on the sample plane are slightly displaced. This means that for proper birefringence measurements, the physical optical path at the two different locations of the sampling beam pair must be known a-priori or be the same to detect the birefringence of the sample. In certain cases, this condition for the sample may not be satisfied and hence in this case, both orthogonal polarized beams must occupy the same exact sampling point on the sample. FIG. 10. shows an embodiment of a spectrally agile heterodyne optical interferometric confocal microscope 60 using a polarization beam displacement prism (BDP) 62 to make the two orthogonal linearly polarized beams 26, 27 collocated at the sample plane. The design and operations are similar to those of microscope 10, but there are some modifications. The light source 12 may be either a tunable laser or a broadband light source. A p-polarizer 63 creates a collimated beam which is coupled to the AOTF 24. After lens 28, the polarizing BDP 62 (e.g., made of Calcite Crystal) is used to combine the two spatially separated p and s-beams and thus make them collinear and overlapping at the exit face of the BDP 62. This polarization beam combining is a unique attribute of the BDP bulk optic. The two beams 26, 27 at the chosen wavelength will have a relative Doppler shift of the AOTF RF drive frequency of $f_c$. Both beams after the BDP enter a beam splitter (BS) 64 that splits the input light power by a desired ratio (e.g., 50:50). Hence, part of the p/s polarizations beam pair passes to a photo-detector 66 in the reference arm of the microscope. A polarizer 68 oriented at 45 degrees to the p and s-directions interferometrically combines the beam pair to produce a reference phase RF signal at $f_c$ that feeds the reference phase port of the RF power meter 40. The other part of the beam pair enters a microscope objective assembly 70 that forms a focused spot (i.e., two spots overlapping each other but of p and s polarizations) on the sample 30 under observation. The sample can be naturally reflective (e.g., human eye) or placed in a holder that contains the bias retarder 32 and mirror 34. The sample reflected light now containing the sample birefringence information for the chosen wavelength returns to the BS 64 via the MO assembly 70 and is directed to the signal path photo-detector 72 that generates the RF signal $f_c$ with the correct sample RF phase. Again, a polarizer 74 at 45 degrees to the p and s directions is used to produce the desired interference signal. Optional lenses 76 and 78 can be used to collect the light efficiently onto the high speed photo-detectors 66, 72, respectively. A confocal pin-hole filter 73 is positioned between the lens 78 and photodetector 72. The signal and reference RF signals at frequency $f_c$ are fed to the RF phase meter 40 that provides both signal amplitude and phase information that gives the sample localized reflectance and birefringence for a given chosen wavelength. Recall that the wavelength is either chosen by tuning the laser and matching the correct AOTF RF drive or using a broadband source and then selecting the correct AOTF RF to select the desired wavelength for optical heterodyne interferometry. Note that the sample can be placed on a rotation, x,y,z motion stage 48 to implement three dimensional (3-D_confocal scanning microscopy when used in conjunction with a pinhole filter placed near photodetector 72. Thus a 3-D scanning heterodyne confocal spectral microscope is formed.

Figure 11:
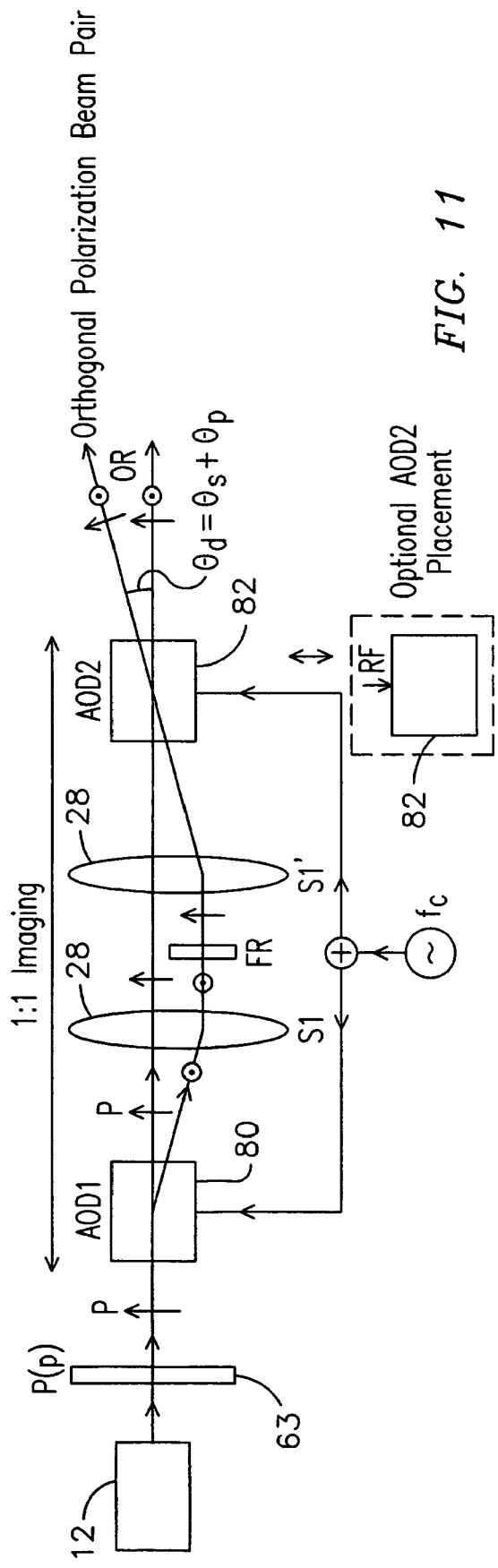
FIG. 11 illustrates an embodiment of a dual-beam generation method using two cascaded AO devices for the spectrally agile heterodyne optical interferometric confocal microscope of FIG. 10.

FIG. 11 shows another embodiment of the dual-beam generation method of FIG. 10 using two cascaded AO devices 80, 82 for the spectrally agile heterodyne optical interferometric confocal microscope. In this case, the BDP 60 is omitted and two AO devices 80, 82 (e.g., AOTF or AO deflector) are used in cascade to generate collinear beams. Note that two sets of collinear beams can be generated with different relative Doppler shifts, based on the orientation of the second AO device 82. One can choose to use one of these beam pairs as input to the MO assembly 70 in FIG. 10. Such a design allows more flexibility for RF selection and optical design for the overall microscope. Note that a benefit of the FIG. 10 and FIG. 11 systems is that phase noise correlated RF signals are fed to the PM 40 resulting in a better signal-to-noise phase detection performance versus an external reference design such as shown in FIGS. 3–5.

The invention claimed is:

1. A confocal microscope comprising:
   a tunable laser source;
   a polarization controller;
   an optical circulator;
   a fiber lens;
   single mode optical fibers coupling light from the laser source, through the polarization controller and optical circulator to the fiber lens;
   an acousto-optic tunable filter positioned to receive light emanating from the fiber lens and adapted to produce a diffracted and a non-diffracted light beams;

a lens positioned proximate the tunable filter and arranged to direct each of the light beams onto a sample to be viewed;

a programmable bias retarder positioned to receive the light beams impinging on the sample;

a mirror proximate the retarder for reflecting the light beams passing through the sample and retarder in a reverse direction through each of the retarder, the sample, the tunable filer and the fiber lens to the circulator; and a photodetector coupled to the circulator for providing a signal representative of the reflected light beams.

2. The microscope of claim 1 and including a polarization device between the fiber lens and tunable filter for passing only p-polarized light.

3. The microscope of claim 2 and including an RF synthesizer for energizing the tunable filter at a desired frequency.

4. The microscope of claim 3 and including a phase meter for comparing the photodetector RF signal to the RF synthesizer signal for synchronization.

* * * * *